United States Patent [19]

Harris

[11] Patent Number: 4,670,914

[45] Date of Patent: Jun. 9, 1987

[54] EYE PROTECTORS

[75] Inventor: Geoffrey W. Harris, Sheffield, United Kingdom

[73] Assignee: National Research Development Corporation, London, England

[21] Appl. No.: 830,878

[22] Filed: Feb. 19, 1986

[30] Foreign Application Priority Data

Feb. 19, 1985 [GB] United Kingdom ............... 8504263

[51] Int. Cl.$^4$ .............................................. A61F 9/02
[52] U.S. Cl. .......................................... 2/436; 2/426
[58] Field of Search ................... 2/436, 426, 428, 435, 2/437, 445, 449, 431

[56] References Cited

U.S. PATENT DOCUMENTS

| | | | |
|---|---|---|---|
| 2,342,766 | 2/1944 | Stiano | 2/437 |
| 2,636,171 | 4/1953 | Aspenleiter | 2/436 |
| 3,000,011 | 9/1961 | Sterne et al. | 2/436 |
| 3,031,675 | 5/1962 | Dubach | 2/437 |
| 3,141,172 | 7/1964 | Hirschmann | 2/436 |
| 3,418,658 | 12/1968 | Danico | 2/436 |
| 3,517,393 | 6/1970 | Beauchef | 2/436 |
| 3,638,240 | 2/1972 | Militello | 2/437 |
| 4,011,595 | 4/1977 | Shields | 2/436 |
| 4,027,342 | 6/1977 | Hirschmann | 2/436 |
| 4,141,085 | 2/1979 | Adams, Sr. | 2/436 |
| 4,264,988 | 5/1981 | Specht | 2/431 |
| 4,435,852 | 3/1984 | Nesler | 2/436 |
| 4,447,914 | 5/1984 | Jannard | 2/436 |
| 4,571,748 | 2/1986 | Carroll et al. | 2/436 |

FOREIGN PATENT DOCUMENTS

| | | | |
|---|---|---|---|
| 77410 | 9/1981 | France | 2/426 |
| 474999 | 8/1967 | Switzerland . | |
| 427434 | 4/1935 | United Kingdom . | |
| 539692 | 9/1941 | United Kingdom . | |
| 603931 | 6/1948 | United Kingdom . | |
| 1180312 | 2/1970 | United Kingdom . | |

Primary Examiner—Werner H. Schroeder
Assistant Examiner—Mary A. Ellis
Attorney, Agent, or Firm—Cushman, Darby & Cushman

[57] ABSTRACT

An eye protector comprising a lens structure spanning a wearers eye in use, a circumambient wall member projecting rearwardly from the lens structure and spacing the lens structure from the wearers face in use while leaving a substantially clear flow path for air across an interior central zone of said eye protector, said wall member having a plurality of ventilation apertures each provided with a rearwardly angled cowl preferably 10 to 20 mm deep and set at from 60° to 90° to the angle of vision and each providing individually a substantially unobstructed ventilation area of at least 80 mm$^2$ e.g. 250 mm$^2$ and in aggregate providing a substantially unobstructed ventilation area of at least 500 mm$^2$ e.g. 1000 mm$^2$ each side of said central zone.

20 Claims, 3 Drawing Figures

EYE PROTECTORS

FIELD OF THE INVENTION

The present invention relates to eye protectors such as goggles.

BACKGROUND TO THE INVENTION

A persistent problem with goggles and with spectacles intended to provide eye protection is their tendency to mist up even under conditions of use that are not particularly arduous. Naturally, the tendency to mist is higher when the wearer is hot and the environment is either cold or damp.

Eye protectors which are substantially enclosed, are frequently provided with ventilating apertures at various positions around their frame periphery but generally these are too small to provide adequate ventilation. For instance, British Patent Specification No. 603931 discloses goggles of the kind having separate eye cups with each eye cup having several small rearward facing cowled openings. The total ventilator area is very small.

In many circumstances, the size of the ventilators is limited by the protective function the eye protectors are required to perform. In an attempt to provide a sufficient level of ventilation without providing too direct a path for the ingress of dangerous materials, turret ventilators, labyrinth ventilators or mesh ventilators are employed. However, we have found that these do little to resist misting, probably because the flow path for air entering and leaving the eye protectors is either too convoluted or too small, giving rise to excessive resistance to flow, or produces an air flow pattern in which air travels around the turret or labyrinth and leaves again without effectively sweeping through the eye protector.

Our research indicates that in order to prevent misting an airflow through an eye protector such as a pair of goggles needs to be at the level of 1 liter to 8 liter per minute, the actual flow rate depending upon the operational circumstances prevailing. In normal indoor working environments ambient wind speeds are not greater than 0.1 to 0.2 m per second since higher wind speeds are likely to cause irritation. In order to obtain an adequate flow rate of air, say 3 liters per minute, through goggles at a linear wind speed of say 0.1 m per second the theoretical unrestricted area of access into and subsequently out of goggles or spectacles must be about 500 mm$^2$ per side. A level of over 1000 mm$^2$ per side of the goggles or spectacles would be desirable.

We have found that existing goggles that provide adequate protection do not provide this level of ventilation. Existing goggles often provide areas of ventilation covered with wire mesh or plastics grill which is inadequate often because of the small size of the individual holes, even if their aggregate area is fairly high. The air flow through a mass of small apertures suffers more resitance than through a larger aperture of the same total area. Except in turbulent conditions, the further the air is from the edge of the aperture through which it flows, the faster it flows. In eye protectors with a large number of small perforations, much of the air flow is slowed by being close to the walls of the perforations.

Moreover, it is often the case that some of the air holes provided are cone shaped with only small exits at the end, some of which are completely sealed over because of poor moulding techniques.

Naturally, it is not possible simply to increase the size of the ventilating holes without rendering eye protectors such as goggles liable to admit foreign material in an undesirable manner.

Another method of avoiding misting which has been proposed in the past is double glazing the lens or lenses of goggles and spectacles. This may help by raising the temperature of the inner lens but because the double glazed lens unit is thicker overall, it may be that the inner lens is brought closer to the face of the wearer thus decreasing the space within the eye protector through which air may flow. This may even make misting worse rather than better.

Anti-mist treatments for lenses or anti-mist compounds which may be applied to lenses do not prevent condensation. They either convert the condensed moisture into a wet rather than a misted layer or absorb the moisture for a short time. This is only satisfactory where there is an intermittent air flow which at its higher level is sufficient to remove the moisture from the lens.

Accordingly, there is a continuing need for a system of ventilation providing large enough, unobstructed apertures to provide adequate ventilation whilst at the same time providing sufficient protection against penetration of dangerous materials into the goggles in common work situations.

BRIEF DESCRIPTION OF THE INVENTION

The present invention provides an eye protector comprising a lens structure spanning a wearers eye in use, a circumambient wall member projecting rearwardly from the lens structure and spacing the lens structure from the wearers face in use whilst leaving a substantially clear flow path for air across an interior central zone of said eye protector, said wall member having a plurality of ventilation apertures each provided with at least one rearwardly angled cowl and each providing individually a substantially unobstructed ventilation area of at least 80 mm$^2$ and in aggregate providing a substantially unobstructed ventilation area of at least 500 mm$^2$ each side of said central zone.

The terms front, back, side, top and bottom used herein to describe and define various features of the eye protectors provided by the invention refer to the eye protectors in the normal wearing position on an erect head.

Preferably, each said ventilation aperture has a substantially unobstructed area of less than about 530 mm$^2$, most preferably about 250 mm$^2$.

Preferably, each cowl has over its entire length a cross sectional area substantially equal to or greater than that of the respective aperture.

Preferably, each aperture and, in cross section, each cowl is generally circular.

Preferably, said apertures and cowls have a diameter of from 10 to 26 mm, e.g. 15 to 21 mm, most preferably about 18 mm.

Preferably, each cowl has a length, measured axially along the longest portion of the interior of the defining wall thereof, of not more than 25 mm, preferably not more than 20 mm, e.g. 10 to 20 mm.

Preferably, the plane of the cowl opening is in each case at an angle of not less than 30° to the optical axis of the eye protector, more preferably, not less than 45°, e.g. 60° to 90°.

Preferably, the ventilation apertures are provided in or toward side portions of said circumambient wall member. Preferably also, the ventilation apertures are provided in bottom portions of said circumambient wall member. Most preferably, apertures are provided in top, side and bottom portions thereof.

There may of course be additional ventilation apertures provided in addition to the cowled apertures described above. Such additional apertures should be adequately shielded against ingress of contaminants.

Preferably, the frame depth provided by said circumambient wall member is at least 20 mm measured at the closest approach of the lens structure to the centre of the wearer's forehead in use, more preferably at least 25 mm, most preferably at least 30 mm.

Preferably, the total ventilation area provided is at least 1500 mm$^2$, more preferably at least 2000 mm$^2$.

Preferably, the lens structure, and optionally said circumambient wall member is double glazed.

The lens structure may comprise a one-piece lens member or may comprise separate lens portions, for each eye, as with spectacles.

Optionally, the ventilation apertures or their associated cowls may be provided with a grid or grille, e.g. of wire, to give added protection against admitting missiles, provided these do not substantially reduce the flow of ventilating air.

DESCRIPTION OF THE DRAWINGS

The invention will be illustrated by the following description of a preferred embodiment with reference to the accompanying drawings in which.

DETAILED DESCRIPTION OF A PREFERRED EMBODIMENT

Figure 1:
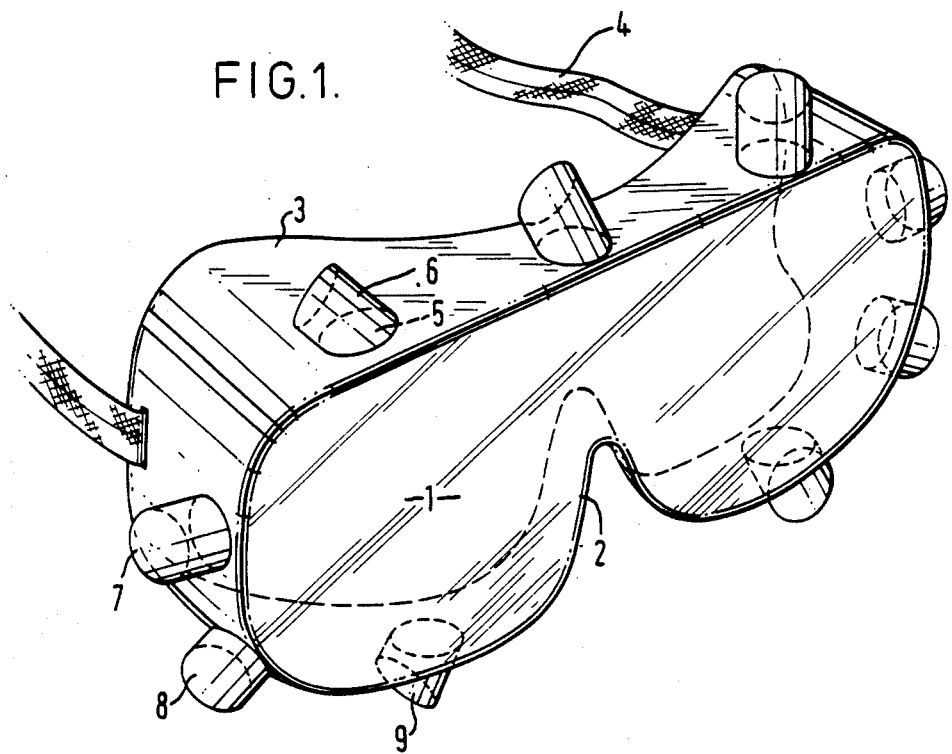
FIG. 1 is a perspective view of a pair of goggles according to the invention.

As shown in FIG. 1, a pair of goggles comprises a lens structure provided by a lens member (1) constituting a one-piece lens including a nose bridge portion (2). Extending rearwardly from the lens member (1) is a circumambient wall member (3) extending around the top, sides and bottom of the lens member. The wall member encloses a central zone and two lateral zones making up the interior of the eye protector, the zones communicating freely for air flow therebetween.

An elastic strap (4) is provided attached at each side part of the circumambient wall (3) for retaining the goggles on the face of a wearer. Whilst this is the preferred form of attachment, a non-elastic strap or side arms could be employed.

Figure 2:
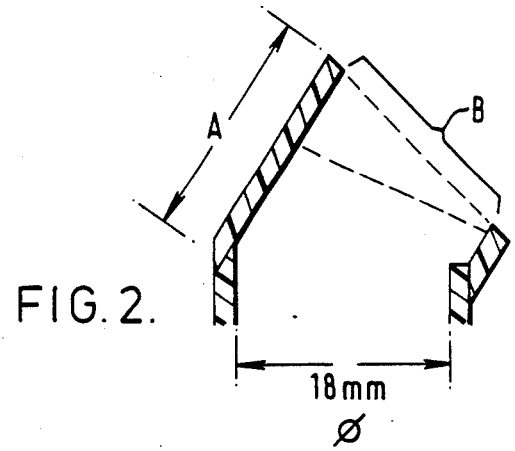
FIG. 2 is a cross-sectional view on the axis of a cowl of the pair of goggles shown in FIG. 1.

Nine ventilation apertures (5) are provided each of which carries a protective cowl (6) which is angled rearwardly from the aperture. As can best be seen in FIG. 2, each cowl is formed from a portion of a right circular cylindrical wall 11 cut along two converging planes. The longest axially extending part of the side wall 11 of the cowl (the dimension A) is different for the different cowls shown. For the three cowls along the top of the wall partly forming the the frame of the goggles, the distance A is approximately 20 mm. For the remaining cowls, the distance is approximately 13 mm. The outer and inner ends 12,13 of each cowl are open The cowl in the centre of the top wall extends upwardly and directly rearwardly and the face of the end of the cowl (marked B in FIG. 2) faces substantially directly backwards along the optical axis of the goggles. The two cowls on either side of the centre cowl of the top wall are angled rearwardly and upwardly and also laterally outwardly by approximately 15 degrees. The two cowls (7,8) at each side of the goggles are angled rearwardly and somewhat downwardly whilst the cowl (9) at either side of the bottom of the goggles is angled rearwardly, downwardly and laterally outwardly by approximately 30 degrees.

The provision of ventilating apertures at the sides of the goggle is particularly valuable as horizontal air draughts are most commonly experienced whilst wearing goggles and these side ventilators enable such draughts to sweep through the goggles to prevent misting.

In still air conditions, convection currents may be established through the lower and upper ventilators.

Each cowl is mounted over a circular ventilating aperture of approximately 18 mm diameter so that each ventilating aperture provides a ventilating area of approximately 250 mm$^2$.

It has been found that a double glazed version of the goggle as described and illustrated is resistant to misting even when there is a differential temperature between the goggle and the wearers face of 32° C. when under comparable test conditions currently available double glazed goggles having as many as four turret ventilators will mist at a temperature differential of as little as 5° C.

Moreover, the goggles described with reference to FIG. 1 will remain mist free under adverse conditions, which in still air would be extremely liable to cause misting, at a much lower level of cross-draught than currently available goggles.

Although the ventilators shown provide a ventilation area of over 2000 mm$^2$ in all and where the ventilation is being provided by large unobstructed apertures, the cowls provide substantial protection against the ingress of dangerous materials into the goggles without preventing free air circulation.

The dimension A of the cowls has been found to be of importance. Lengthening the cowls illustrated by as little as 3 mm has a substantial effect upon the effectiveness of the ventilation and causes the double glazed goggles to mist under standard test conditions at a differential temperature of six degrees less than can be sustained using the dimensions described above.

Since the risk of materials being projected towards the goggles is greatest in the case of materials falling from above, the cowls at the top of the goggles are the most rearwardly directed.

Figure 3:
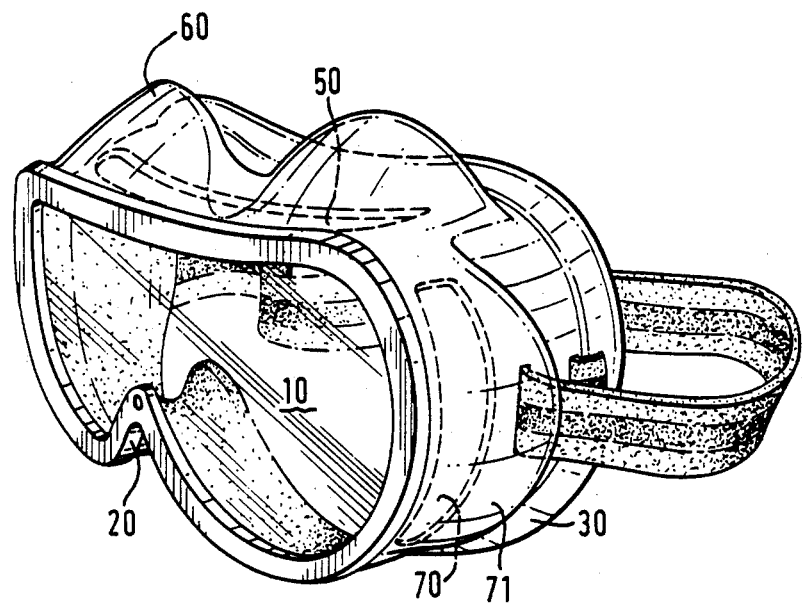
FIG. 3 is a perspective view of a second embodiment of the invention.

With reference to FIG. 3, there is shown a second embodiment according to the invention in the form of a pair of goggles having a lens member 10 extending across both of a wearer's eyes in use and mounted in a front frame including a nose bridge portion 20, and a circumambient wall member 30 extending rearwardly from the front frame and the lens member 10. Circumambient wall member 30 is provided with ventilation apertures of which two are visible in the figure. Ventilation aperture 50 is an elongate slot extending across essentially all of the length of the top part of the circumambient wall 30 whilst aperture 70 is a circumferentially elongate aperture in the form of a slot extending around the curved side portion of the goggles. A corresponding aperture to that shown as aperture 70 will be provided in the opposite side portion of the goggles.

A pair of cowls 60 are provided together overlying the aperture 50 in the top wall. A single cowl 71 overlies the aperture 70. Each of the cowls illustrated differs from those illustrated in FIG. 1 in that instead of the base of the cowl being a circle, it is open to the rear. The cowls are formed generally as portions of domed blisters with the ends 62 and 72 of the cowls 60 and 71, respectively, facing away from the ventilation aperture being open. As can be seen, the apertures provided are relatively large and easily provide individually a ventilating area greater than 80 mm$^2$ and in aggregate provide a ventilation area substantially in excess of 500 mm$^2$ on each side of the centre.

Naturally, all conventional methods of reducing misting may be employed such as the use of a double glazed lens, anti-misting compositions or anti-misting lens materials.

In both illustrated embodiments, since the circumambient frame member is deep relative to that of most goggles it is particularly advantageous to blacken, or in other another manner make opaque, the top surface of the frame member to reduce light scattering from the lens.

Whilst the invention has been described with reference to particular characteristics of the preferred embodiment illustrated in the drawings, many modifications and variations are possible within the scope of the invention. For instance, whilst the invention has been described with reference to goggles, it may also be applied to spectacles, i.e. eye protectors in which separate lenses are provided for each eye.

The eye protectors illustrated may be constructed of materials conventionally used such as transparent plastic materials.

I claim:

1. An eye protector comprising a lens structure spanning a wearers eye in use, a circumambient wall member projecting rearwardly from the lens structure and spacing the lens structure from the wearers face in use whilst leaving a substantially clear flow path for air across an interior central zone of said eye protector, said wall member having a plurality of ventilation apertures each provided with a rearwardly angled cowl and each providing individually a substantially unobstructed ventilation area of at least 80 mm$^2$ and in aggregate providing a substantially unobstructed ventilation area of at least 500 mm$^2$ each side of said central zone.

2. An eye protector as claimed in claim 1 wherein each said ventilation aperture has individually a substantially unobstructed area of at most 530 mm$^2$.

3. An eye protector as claimed in claim 2 wherein each said ventilation aperture has individually an unobstructed area of about 250 mm$^2$.

4. An eye protector as claimed claim 1 wherein each cowl has over its entire length a cross-sectional area at least substantially equal to that of the respective aperture.

5. An eye protector as claimed in claim 1 wherein each aperture and, in cross section, each cowl is generally circular.

6. An eye protector as claimed in claim 5 wherein each aperture and cowl has a diameter of from 10 to 26 mm.

7. An eye protector as claimed in claim 6 wherein each aperture and cowl has a diameter of from 15 to 21 mm.

8. An eye protector as claimed in claim 7 wherein each aperture and cowl has a diameter of approximately 18 mm.

9. An eye protector as claimed in claim 1 wherein each cowl has a length, measured axially along the longest portion of the interior of the defining wall thereof, of at most than 25 mm.

10. An eye protector as claimed in claim 9 wherein said measurement is at most than 20 mm.

11. An eye protector as claimed in claim 10 wherein said measurement is from 10 to 20 mm.

12. An eye protector as claimed in claim 1 wherein the plane of the exterior opening of each cowl forms an angle of at least 30 degrees to the optical axis of the eye protector.

13. An eye protector as claimed in claim 12 wherein said angle is at least 45 degrees.

14. An eye protector as claimed in claim 13 wherein for a substantial proportion of said cowls said angle is from 60 degrees to 90 degrees.

15. An eye protector as claimed in claim 1 wherein at least one of the ventilation apertures is provided in each of the two opposed side portions of said circumambient wall member, at least one of said ventilation apertures are provided in a bottom portion of said circumambient wall member and at least one of said apertures is also provided in a top portion of the circumambient wall member.

16. An eye protector as claimed in claim 1 wherein the circumambient wall member is such as to provide a frame depth of at least 20 mm measured at the closest approach of the lens member to a wearer's forehead in use.

17. An eye protector as claimed in claim 16 wherein said measurement is at least 25 mm.

18. An eye protector as claimed in claim 17 wherein said measurement is at least 30 mm.

19. An eye protector as claimed in claim 1 wherein the total ventilation area provided is at least 1500 mm$^2$.

20. An eye protector as claimed in claim 19 wherein said ventilation area is at least 2000 mm$^2$.

* * * * *